United States Patent [19]

Baker et al.

[11] 4,052,431
[45] Oct. 4, 1977

[54] PROCESS FOR THE PRODUCTION OF COMMERCIAL ALPHA OLEFIN SULFONATES

[75] Inventors: Thomas G. Baker, Wilmette; Raymond J. Shute, Chicago, both of Ill.

[73] Assignee: Stepan Chemical Company, Northfield, Ill.

[21] Appl. No.: 663,611

[22] Filed: Mar. 3, 1976

[51] Int. Cl.² .................. C07C 139/14; C07B 13/02
[52] U.S. Cl. ............................... 260/513 T; 260/400
[58] Field of Search ........................ 260/513 T, 400

[56] References Cited

U.S. PATENT DOCUMENTS

| | | | |
|---|---|---|---|
| 3,169,142 | 2/1965 | Knaggs et al. | 260/457 |
| 3,409,637 | 11/1968 | Eccles et al. | 260/513 T |
| 3,420,875 | 1/1969 | De Salvo et al. | 260/513 T |
| 3,424,694 | 1/1969 | Stein et al. | 260/513 T |
| 3,531,518 | 9/1970 | Ohren et al. | 260/513 T |
| 3,634,287 | 1/1972 | Woo | 260/513 T |
| 3,639,282 | 2/1972 | Sharman | 260/513 T |

Primary Examiner—James O. Thomas, Jr.
Assistant Examiner—James H. Reamer
Attorney, Agent, or Firm—Hill, Gross, Simpson, Van Santen, Steadman, Chiara & Simpson

[57] ABSTRACT

Alpha olefin sulfonates generally commercially made by reacting $SO_3$ with alpha olefins followed by neutralization and saponification with base (typically sodium hydroxide), and subsequently bleaching, characteristically may contain by-product impurities which are non-sulfonate sulfur containing organic compounds. These impurities chiefly sultones, can be substantially completely eliminated by the process sequence of the present disclosure which involves heating and bleaching and pH adjustment under specified conditions. Surprisingly, such and similar organic sulfurous impurities are eliminated during such heating and do not reform under such bleaching and pH adjustment.

12 Claims, 2 Drawing Figures

PROCESS FOR THE PRODUCTION OF COMMERCIAL ALPHA OLEFIN SULFONATES

BACKGROUND OF THE INVENTION

Alpha olefin sulfonates are commonly manufactured by reacting alpha olefins with sulfur trioxide utilizing falling film technology as taught by Knaggs et al U.S. Pat. No. 3,169,142 followed by neutralization in an aqueous medium containing alkali metal hydroxide. In addition to alkali metal sulfonates, the initial resulting product also characteristically contains unreacted olefins and sulfur containing organic components, chiefly sultones, which are not alkali metal sulfonates.

For purposes of maximizing conversion levels of alpha olefins to alpha olefins sulfonates, of minimizing to the point of elimination the presence of non-sulfonate sulfur containing components, and of bleaching, since such intermediate products are characteristically too dark in color for commercial acceptability, and so must be bleached, prior art alpha olefin sulfonate manufacturing technology fails to provide adequate teachings or suggestions. When bleaching is undertaken by the prior art technology, sulfur containing organic components which are not alkali metal sulfonates are actually produced as by-products, adding to any undesirable components already present.

In the present context (except where stated or implied in a narrower sense) the term "alpha olefin sulfonate(s)" is used in its broadest commercially accepted sense to include not only 1,2-alkene-1-sulfonates, but also generally a broad mixture of alkenyl sulfonates, hydroxyalkane sulfonates, poly (primarily -di-) sulfonates, hydroxy alkenyl sulfonates, and similarly related sulfonates; such so-called commercial alpha olefin sulfonate products also contain quantities of hydrocarbons, alpha olefins and isomerized olefins, aliphatic alcohols, and lesser quantities of other by-products and unreacted matter, as well as, inorganic species, all in an aqueous system.

BRIEF SUMMARY OF THE INVENTION

The present invention is directed to an improved process for making the biodegradable alpha olefin sulfonates surfactants. A primary aim of this invention is to substantially completely eliminate all sulfur organic components in an alpha olefin sulfonate product which are not alkali metal sulfonates. Since the vastly predominant sulfur containing non-sulfonate species, and the most difficult to eliminate sulfur containing non-sulfonate species are sultones, a primary air of this invention is to provide a process adapted for substantially completely eliminating sultones in an alpha olefin sulfonate product.

Another air of this invention is to substantially completely eliminate the presence of all sulfur containing organic by-product components, sultones, which might otherwise be present in a bleached alpha olefin sulfonate product by converting such components into alkali metal sulfonates, and also by preventing the redevelopment of such by-products, and other similar product components, in such a bleached product.

One achievement of this invention is a maximum of the conversion of sulfonated alpha olefins to sulfonates in the manufacture of alpha olefin sulfonate detergents.

Another aim of this invention is to provide an alpha olefin sulfonate product containing substantially no sulfur containing organic components which are not alkali metal sulfonates. Such non-sulfonate sulfur containing components serve no functional purpose and not only tend to reduce the level of desired sulfonates in a given surfactant, but, in addition, such sulfur containing organic components, at least in some instances, can exert undesirable effects upon alpha olefin sulfonate products. For example, certain sulfur containing organic components act as antifoam agents if present in sufficient quantities. Further, certain such sulfur-containing components can slowly hydrolyze causing product pH shifts.

The invention provides a bleaching technique for aqueous alkali metal sulfonates which have been previously treated to substantially eliminate all sulfur containing organic components in such an alpha olefin sulfonate material, which components are not alkali metal sulfonates. Not only is the reformation of such non-sulfonate impurities surprisingly substantially completely prevented during bleaching, but also the bleaching efficiency of a bleach, such as sodium hypochlorite, is unexpectedly improved.

The invention further provides a technique whereby, first, by the action of heat, all sulfur containing organic components in an alpha olefin sulfonate product which are not alkali metal sulfonates are substantially completely eliminated, and then this resulting product in a specified reaction sequence by the action of a combination including bleach, pH, and temperature, is lightened in color substantially without reforming or generating any sulfur containing organic components in such alpha olefin sulfonate product, which components are not alkali metal sulfonates.

Another aim of the invention is to eliminate from alkali metal alpha olefin sulfonate products sulfur containing impurities belonging to the class of organic compounds known generally as sultones because such compound class, or members thereof, may have undesirable side effects, including some as indicated earlier.

Other and further objects, aims, purposes and advantages of the present invention will be apparent to those skilled in the art from a reading of the present specification taken with the accompanying drawings.

More specifically, the present invention relates to an improvement in a process for making alpha olefin sulfonates by the known prior art method of first contacting a stream of vaporized sulfur trioxide diluted with an inert gas, usually air, with liquid alpha olefins containing from about 8 through 24 (preferably from about 12 through 18) carbon atoms per molecule followed by admixture of the reaction product with aqueous alkali metal hydroxide. In the process of the present invention, the resulting aqueous liquid phase system is heated at a temperature of from about 95° to 190° C (preferably from about 150° to 180° C) while maintaining such system under autogenous pressure of from about atmospheric to about 230 psig (preferably from about 120 to 160 psig) for a time sufficient to substantially completely eliminate sulfur from residual oil in such system (which means, in effect, that all non-sulfonate sulfur containing organic compounds have been substantially eliminated from such system). Such heating is conducted while maintaining sufficient dissolved free alkali metal hydroxide present in such system at a level to produce a system pH in the range of from about 12.0 to 14.0 (and preferably in the range of from about 12.3 to 13.0).

Thereafter, one cools the resulting so-heated system to a temperature below about 60° C (and preferably below 5° C) and then contacts such so-cooled system under liquid phase aqueous conditions with the bleaching agent sodium hypochlorite. The total amount of such bleaching agent (active ingredient basis) used ranges from about 0.1 to 6 weight percent of the total weight of alkali metal sulfonated products present in such resulting so-heated system (and preferably from about 0.5 to 2.0 weight percent). Such contacting is conducted while maintaining such resulting so-heated system at a pH in the range of from about 12.0 to 14.0 (and preferably from about 12.3 to 13.0). Also, such contacting is further conducted while maintaining such resulting so-heated system as a temperature of from about 25° to 60° C (and preferably from about 35° to 50° C). Such contacting is conducted for a time sufficient to produce a Klett color of about 180 or less (and preferably about 130 or less) at 5 weight percent total sulfonate of alpha olefin sulfonate in water. Such contacting is conducted as a practical matter for a time which is either sufficient for complete reaction of added sodium hypochlorite with color bodies or is sufficient for achievement of a desired product color level. Excess bleach remaining after a bleaching operation optionally can be destroyed by the addition to bleached product of an antichlor (reducing agent), such as sodium sulfite, sodium bisulfite, or the like. Subsequent product pH adjustment may be desirable. If, in fact it is intended to adjust the product pH to a lower level, it is necessary to first completely react or destroy all residual bleaching agent prior to pH adjustment with acids (such as sulfuric and the like), as those skilled in the art will readily appreciate.

DETAILED DESCRIPTION

Figure 1:
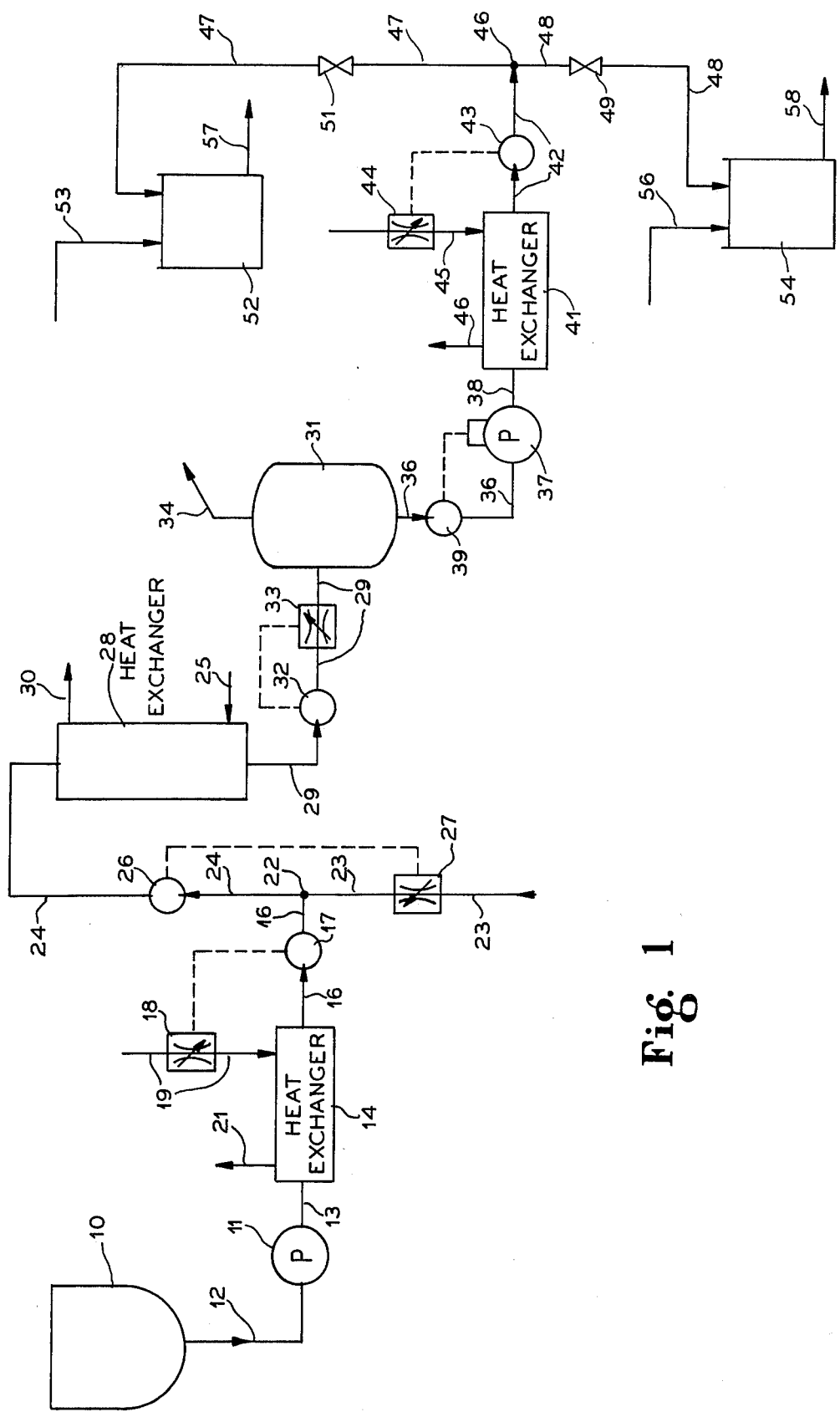

As those skilled in the art will appreciate, to make alpha olefin sulfonates, one reacts a stream of vaporized sulfur trioxide diluted with an inert gas such as air, $SO_2$, etc., with liquid alpha olefins in a continuous film reactor. The mole ratio of sulfur trioxide to alpha olefins employed in such reactions is from about 1.0 to 1.2. This acid reaction product is allowed to age for a brief period of time, usually under about 10 minutes, so as to allow isomerization of undesirable components, such as materials which, when neutralized/saponified, lead to water insoluble substances, such as sodium salts of 2-hydroxy sulfonates, as those skilled in the art will appreciate. Then, thereafter, one discharges such a vapor phase acid reaction product into an aqueous alkali metal hydroxide (preferably sodium hydroxide) system to form a suspension containing sufficient alkali to allow for complete neutralization and ultimately substantially complete saponification.

Thus, a starting material used in the practice of the present invention comprises an aqueous solution or dispersion (herein generally termed a suspension) in which is contained an alpha olefin sulfonate material (which itself is a complex mixture of different molecules), dispersed organic oil-like components, and unreacted alkali metal hydroxide. A portion of the oil-like components are to be considered minor components (usually not more than 3 to 5 weight percent of total starting material), and generally these are not functional components in the practice of the present invention and do not contain sulfur.

The total quantity of such dispersed organic oil-like components, termed residual oil, relative to the total weight (on a dry solids basis) including sulfonate alkali metal salts present in the aqueous phase, may range from an amount which is as little as about 5 weight percent up to about 40% by weight (typically, in common commercial operations, from about 5 to 30 weight percent), through somewhat higher or lower quantities may be present, depending upon such variables as reaction conditions, equipment considerations, and other factors. Under normal operating parameters on a commercial scale, as those skilled in the art will appreciate, the quantity of sulfonate product present in such aqueous alkaline system typically ranges from about 50 to 90 weight percent (based upon dry solids), through higher and lower quantities may be present depending upon similar variables to those above mentioned. The balance of the dry solids content of the starting material is substantially comprised of the added free alkali metal hydroxide. The usual alkali metal employed in the process of this invention is sodium, and sodium hydroxide is preferred for use in the practice of this invention. The balance of up to 100 weight percent of a given starting material can be considered to comprise water. Usually the amount of water present in a given starting material is not less than about 52 weight percent (same total weight basis) but larger or smaller amounts may be present.

The non-sulfonate components which contain sulfur and which are present in a starting material used in the practice of the present invention, or whose presence or absence in a product produced by the practice of the present invention (or in an intermediate therefor) may be determined by any convenient method of analysis. However, one convenient and preferred analytical procedure involves an analysis of the residual oil present which is derived by the synthetic route above indicated.

The composition of the residual oil in a starting material comprises mainly various sulfur-containing reaction products and unreacted alpha olefin starting material. The origin and composition of starting materials used in the practice of the invention can vary, as those skilled in the art will appreciate. Such sulfur-containing reaction products are complex in nature and in distribution, but are not simple alkali metal sulfonates. Analysis suggests that such sulfur-containing by-products comprise, mainly, sultones, through other olefin-derived sulfonate esters may be present. In any given residual oil system, the relative percentages of unreacted alpha olefins and total sulfur-containing by-products can vary, the exact relative quantities of each such major component in any given system being dependent upon reaction conditions and other variables. Typically, and for purposes of illustration only, quantities of olefins (including, but not limited to, alpha olefins) present in such a residual oil have been observed to range from about 5 to 60 weight percent, while, correspondingly, quantities of such sulfur-containing by-product components in such residual oil have been found to range from about 35 to 95 weight percent (on a 100 weight percent total residual oil basis), through larger and smaller respective quantities of these components have been observed and may be present in a particular residual oil. Other materials may also be present in the residual oil typically in amounts less than about 20 weight percent (same basis) which components are not typically sulfur-containing.

For the purpose of the present invention, residual oil present in an alpha olefin/sulfur trioxide reaction product can be determined by any conventional procedure. Thus, to determine the quantity of residual oil present in a given alpha olefin sulfonate material involved in the practice of the process of the present invention, one preferred procedure, for illustration purposes, comprises taking 10 grams or so of a sample of such a material (e.g., a starting material or, a reaction product from some stage in the practice of the process of this invention, or the like, as the case may be), and then, to this 10 grams, adding from about 100 to 150 milliliters of a 50/50 ethanol/distilled water mixture. To the resulting mixture is then added about 30-50 milliliters of a hydrocarbon solvent, for example, a petroleum ether having a boiling range of from about 30° to 60° C. This product mixture is agitated and allowed to separate. The petroleum ether layer (the upper layer) is separated and collected. The extraction procedure just indicated is typically repeated about four to five times and the resulting petroleum ether fractions are combined, and the petroleum ether evaporated to dryness leaving a residual oil. (Alternatively, residual oil may be isolated by ion-exchange techniques.) This residual oil is then subjected to testing as desired to determine its composition and other properties.

For the purpose of this invention, the quantity of sulfur-containing organic components in a residual oil which are not alkali metal sulfonates, and which are present in, for example, a starting material used in the practice of this invention, may be determined by any of a number of conventional analytical procedures for specific chemical entities or even by total sulfur analysis. For example, the total organic sulfur in the residual oil, one may use the Carius method or the oxygen bomb method (ASTM Method Test No. D129-64), or the like. (If one chooses to determine total organic sulfur in the residual oil it may be necessary to apply a correction for any sulfonates extracted into the oil or to first eliminate them by, for example, ion-exchange chromatography). Specific entities such as sultones may be determined by infrared spectroscopy or chromatographic methods or other suitable methods. For purposes of this invention, the quantity of alkali metal sulfonate present in a particular system (such as a starting material or a heated bleached product, or intermediate system) may be determined or estimated by any conventional analytical procedure. For example, one may use the paratoluidine hydrochloride method (as described in M. J. Rosen and H. A. Goldsmith's "Systematic Analysis of Surface-Active Agents", Wiley-Interscience), or the like. However, it is not common practice to assay a starting material for sulfonate content nor for sulfur-containing species in a residual oil of a starting material on a routine basis. Such analysis might be performed for research or background purposes.

The alpha olefin feedstocks used to make alpha olefin sulfonates are typically complex mixtures of various olefinic materials containing from about 8 through 24 carbon atoms per molecule, and preferably from about 12 through 18 carbon atoms per molecule. Such mixtures of alpha olefins are available commercially from a variety of manufactures.

Alpha olefins are sulfonated conventionally and commercially by contact with an inert gas (usually air) diluted stream of vaporized sulfur trioxide in continuous thin film reactors. Molar ratios of sulfur trioxide to alpha olefin feedstock of greater than one are typically employed (usually 1.0 to 1.2). Such sulfonation conditions are known to the prior art and do not constitute a part of the present invention. The reactions involved are complex and lead to mono- and poly-(primarily di-) substituted products, as well as residual unsubstituted products. The major initial products are apparently sultones, alkenylsulfonic acids, disulfonic acids, sultone acids and unreacted olefins, although significant amounts of other products are also produced. Numerous publications on various aspects of alpha olefin sulfonate manufacture exist. Recently, it has been postulated that acid sulfonate esters (sometimes called oligomer acids) may be formed by sulfonic acid addition across olefinic double bonds of other sulfonic acids. Neutral sulfonate esters may be formed by sulfonic acid addition across appropriate double bonds of unsulfonated olefins. Alpha olefin systems contain small quantities of less reactive internal and branched olefins, and unreactive paraffins, and other materials, these materials will sometimes tend to accumulate in somewhat higher proportions in the unreacted oil fraction than they are found in the feedstock. However, in addition, alpha olefins may undergo some isomerization during such a sulfonation reaction to internal isomers, as well as undergo some polymerization. The composition of an acid mixture formed by reacting sulfur trioxide with alpha olefin may change with time. For example, 1,2-sultones are known to rapidly (minutes or less) isomerize to 1,3-sultones and 1,4-sultones. Also, the overall sultone of an acid mixture may increase on storage at the expense of an alkenylsulfonic acid, although such reaction appears to be slow. Hydrocarbons isolated from freshly sulfonated alpha olefins, for example, may contain from 10 to 20 weight percent internal olefin, but after aging, internal isomers typically appear to be more prevalent. Generalizations are difficult to make.

A starting material used in the practice of the present invention typically contains, in addition to alpha olefin sulfonate, residual oil and water, as described above, on a 100 weight percent total weight basis, from about 1.0 to 6.5 weight percent of added, unreacted, alkali metal hydroxide. The pH of a starting material is typically greater than about 12.

It must be remembered that a starting material is this invention is, in fact, a very dynamic system capable of continuing reaction(s), and that exact compositional assays will vary depending upon many factors of previous history, such as time and temperature of handling before analysis, and the like. Furthermore, although the overall process is considered and described stepwise, because of the very dynamic nature of the system, processing steps can and do occur simultaneously/concurrently. For example, some hydrolysis does not occur during the neutralization step. The degree to which this occurs depends on the various environmental parameters involved.

In accordance with the teachings of this invention, such a starting material is heated under the controlled conditions above-indicated. The effect of this heating is to hydrolyze and to saponify the sulfur-containing organic components which form a portion of the residual oil, as above-described which increases the yield of alkali metal sulfonates. Such heating of, for example, sultones, yields alkali metal alkenylsulfonates and alkali metal hydroxyalkanesulfonates. The distribution of these new respective alkali metal sulfonate products relative to each other depends upon the exact heating conditions. Thus, for example, heating under mild, basic conditions tends to favor formation of alkali metal hydroxyalkanesulfonates, while heating at elevated temperatures tends to favor formation of alkali metal alkenylsulfonates. Usually both types of reaction occur simultaneously to some extent. The heating causes the 1,3 and 1,4-sultones to convert into, respectively, the alkali metal 3-hydroxy- and the 4-hydroxyalkanesulfonates, together with the corresponding alkali metal alkenylsulfontes. If present, sultone sulfonic acids presumably convert to the alkali metal hydroxyalkane and the alkenyl disulfonates on heating. The alkenylsulfonic acid oligomers apparently yield alkali metal hydroxyalkanesulfonates and alkenylsulfonates on heating. Neutral sulfonate esters hydrolyze to yield alkali metal sulfonates and secondary alcohols, or, possibly, sometimes, olefins, depending on heating conditions.

Hydrolysis rates of the various sulfur-containing species present in a starting material are such that the mot difficult to hydrolyze/saponify compound class is that of 1,4-sultones (delta sultones); hydrolysis/saponification reactions of other sultones and sulfonate esters and more facile, that is, they proceed to substantial completion with greater speed. Consequently, completion of a heating step in accordance with this invention is demonstrated, for example, by the substantially total absence of the sulfur-containing compound class, 1,4-sultones, from residual oil, and is routinely accomplished a shown by analysis. For instance, in a continuous standarized heating operation, operating within specified predetermined conditions, the quantity of sulfur-containing non-sulfonate compounds present in a starting material is generally known to decrease during the heating period and the heating conditions and times can be selected so as to be assured that such non-sulfonate sulfur-containing compounds initially present in a starting material are substantially completely removed by hydroylsis and/or saponification during the heating step, as desired.

In general, as the temperature and/or pressure employed during a heating step increases, the time required for heating diminishes, other considerations remaining constant. The exact combination of temperature and pressure employed in any given situation is, naturally, a function of the equipment available, particularly as regards pressure considerations. For example, in a batch-type heating operation, a conventional kettle-type reactor can be maintained at essentially atmospheric pressure and somewhat above, and the kettle contents can be heating up to temperatures ranging from about 110° to 120° C. (preferably about 113° to 118° C.). Heating time under such conditions can range from about 4 to 8 hours, typically. Higher temperatures and autogenous pressures may advantageously be employed, particularly in batch-type hydrolysis sequences, if suitable equipment capable of taking the additional stresses involved is available. However, equivalent heating action can be achieved by passing continuously a system being heated through a tubular-type reaction zone wherein the temperature is maintained in the range from about 150° to 180° C., and the pressure is maintained in the range from about 120 to 160 psi, the residence time of such system in such zone being typically and preferably for commercial reasons under about 30 minutes. Combinations of batch and continuous heating sequences may be employed. Regardless of procedure, however, heating is conducted for a time sufficient to substantially completely eliminate sulfur-containing species from the residual oil characteristically present in a starting material used in this invention. Characteristically, the residual oil which remains after such a heating sequence is comprised mainly of saturated and unsaturated hydrocarbons and saturated aliphatic alcohols. These alcohols characteristically contain one hydroxyl group per molecule. Very minor amounts of other components may be present.

As indicated, the quantity of residual oil in a starting material can vary over a wide range. If, for example, standarized operating conditions are not maintained in reacting $SO_3$ with alpha olefins, the amount of residual oil present in a starting material can rise, usually on a temporary basis, until the process is again operating within specified program parameters.

While, as those skilled in the art will appreciate, sulfur-containing oily products resulting from reaction of alpha olefins with $SO_3$ do slowly react with aqueous alkali metal hydroxide. However, the practical purposes, this reaction is, essentially, too slow for commercial utilization at about typical neutralization temperatures.

To determine free alkali metal hydroxide content and expected excess free alkali metal hydroxide content in hydrolyzed starting material, samples of starting material can be taken and analyzed conventionally, and additional alkali metal hydroxide added if necessary to maintain a desirable excess of free alkali metal hydroxide content. While one can rely upon a test such as ethylene glycol reflux acidity to determine, for example, residual expected caustic content after hydrolysis/saponification, such test seems to give slightly low results perhaps due to the difficult-to-hydrolyze 1,4-sultone isomers which may be present. Additionally, and more reliably, one rely upon a laboratory scale high temperature, high pressure hydrolysis procedure, as for example, employing a Parr bomb.

Hydrolysis equipment permitting employment of higher temperatures and pressures allows for achievement of reduction/elimination of sulfur-containing materials from residual oil in generally shorter times than with lower temperatures and lower pressure batch hydrolysis conditions, as for example, with certain pressure limited reaction vessels. In general, lower temperatures appear to require substantial additional heating time in order to achieve equivalent results.

The product resulting from such heating step is typically sufficiently dark in hue as not to be desirable from a commercial point of view. Such darkening occurs because, during sulfonation, much heat is generated (sulfonation being a strongly exothermic process), air is present (typically), and oxidation occurs characteristically inherently as evidenced by $SO_2$ evolution, so that color degradation results. Consequently, it is necessary and desirable from a commercial point of view to bleach the heated alkali metal alpha olefin sulfonate product in commercial production in order to obtain surfactants in suitable color.

In a preferred mode of practicing this invention, one adds about 0.5 to 2.0 weight percent active bleach (based on total alkali metal sulfonate present) to a batch of liquid product produced by the present teachings. In a commercial operation, standardized procedures are preferably used, and the total quantity of alkali metal sulfonate present ranges from about 30 to 45 weight percent (based on total system weight). Thus, in such an operation, one adds bleach based on about 30 to 45 percent of alkali metal sulfonate.

The exact amount of bleach employed in any given bleaching operation is, of course, to some degree dependent upon the color of the previously heated system to be bleached. A very dark system thus would require more active bleach than one which happens to be light in hue. When using a bleaching agent, such as sodium hypochlorite, the process of bleaching inherently introduces into the system being bleached chloride ions which turn up in a final product as alkali metal chlorides. For certain detergent formulating and end use purposes and other considerations, as those skilled in the art will appreciate, it is desirable to limit the total amount of chloride ions present in a product. Preferably, a bleached product of this invention contains from about 0.4 to 1.0 weight percent alkali metal chloride (total dry weight basis) although more or less may be present depending upon bleach requirements.

The process used for bleaching of a starting material heated in accord with the teachings of this invention is critical since various sulfur-containing non-sulfonate impurities, such as sultones, are readily regenerated in such previously heated system under certain bleaching conditions, surprisingly. Unexpectedly, if bleaching of such previously heated system is accomplished using the conditions, especially the pH conditions, taught and provided by the present invention, substantially no reformation of such sulfur-containing impurities occurs.

It has now been discovered that apparently the singlemost critical parameter in alpha olefin sulfonate bleaching, as respects materials such as sultones, is that of pH. Thus, while it is possible to completely remove by heating substantially all sultone isomers in an alpha olefin sulfonate starting material, normal production bleaching techniques known to and used in the prior art lead to their reformation. However, if the pH is made to be at a suitable high level during the bleaching, sultone reformation does not occur in an alkali metal alpha olefin sulfonate product. If this proper pH level is not present during bleaching, for example, a previously heated alkali metal alpha olefin sulfonate material which initially contains no by-product sulfur-containing compounds in its residual oil, such material will regenerate sultones and possibly certain other sulfur-containing organic non-sulfonate species.

If a suitable high level pH is maintained during bleaching, there seems to be little, if any, temperature dependence upon, for example, sultone generation. In other words, if a proper high level pH is maintained, bleaching may be accomplished at higher temperatures or lower temperatures without, for example, sultone production or reformation.

A product alkali metal alpha olefin sulfonate material which contains substantially no sulfur in its residual oil and which has been bleached in accordance with the teachings of this invention typically needs to have is pH adjusted downwardly so as to bring it into pH ranges commonly enountered in, and desired for, commerce. Since the addition of acid in the presence of bleach (such as NaOCl) is strictly deleterious and leads to formation of sulfur compounds such as sultones and derivatives and/or analogues thereof, for example, it is necessary to first add an antichlor (e.g., a reducing agent) prior to pH adjustment if residual bleach is present. In the prior art, pH adjustments have apparently usually been made in the presence of residual bleach (such as NaOCL), especially where large amounts of bleach were required to improve product color to commercially acceptable levels. In accord with the teachings of the present invention, when a suitable color is obtained or achieved in a given alkali metal alpha olefin sulfonate product system by bleaching as taught herein, bleaching may be terminated, but it is much preferred to add an antichlor to this bleached system to react with residual bleach rather than to wait for complete reaction of the bleach before adding acid to the system in order to reduce product system pH to a desired level. Typical commercial pH values for alkali metal alpha olefin sulfonate material fall in the range from about 7 to 12, more commonly about 7 to 10, as those skilled in the art will appreciate.

While any conventional antichlor may be employed, alkali metal sulfites are preferred, such as sodium sulfite, sodium bisulfite, or the like. It is preferred to add such antichlors in the form of a concentrated aqueous solution, or less preferably, as aqueous slurries.

Typically, it takes more than a stoichiometric amount of sulfite to completely react with residual bleach (such as sodium hypochlorite) remaining in a product following a bleaching operation if residual bleach is present. The stoichiometry of this reaction is of an indeterminate nature, characteristically, and depends upon rate, and order, of addition of reagents, pH, temperature and similar variables. This indeterminate phenomenon is an example, apparently, of chemical induction and, although this phenomenon is known and documented in chemical literature (see for example, I. M. Kolthoff and V. A. Stenger, "Volumetric Analysis," Volume I, Interscience Publishers, Inc.), it is not fully understood in the present circumstances.

Acid used for final pH adjustment after a bleaching operation is preferably in an concentrated aqueous solution form. Acids suitable for use in the practice of the present invention for adjusting the pH of a bleached product which contains no residual bleach include, for example, sulfuric acid, hydrochloric acid, phosphoric acid, citric acid and the like. Usually such acid is used in the form of a concentrated aqueous solution. For example, a preferred acid solution is about 50% aqueous sulfuric acid.

The bleaching may be practiced using batch operating conditions, continuous operating conditions, or mixtures thereof, under pH conditions as indicated above. For example, batch bleaching may be accomplished using temperatures in the range from about 25 to 60° C. and at atmospheric pressure. Batch bleaching times using such conditions typically range from about 2 to 8 hours longer an shorter times may be used.

Continuous bleaching conditions typically involve similar pH's, temperatures, pressure, and bleaching times as employed in batch operations. Although bleach addition may be a continuous operation, it is normal for at least part of the bleaching to continue to complete while the material is held in a finishing batch holding tank.

Bleaching agent can be added as pratical during a bleaching operation, but, particularly in batch operations, it is presently preferred to add the bleaching agent as rapidly as in practical based on equipment considerations at the start of a bleaching operation. The guiding criterion is that no local excesses of bleaching agent should be allowed to build up upon addition of the bleach. Thus, if mixing equipment only allows for poor to fair mixing, the addition of bleaching agent should be relatively slow. With proper mixing, the addition of bleaching agent can be accomplished reasonably rapidly.

After sufficient bleaching has been conducted, one way to conveniently test a given batch for residual hypochlorite content is by using the conventional potassium iodide solution test procedure, through any convenient technique can be used. To eliminate residual hypochlorite an antichlor is added to the batch. Usually, for every 0.01 weight percent (total weight basis) sodium hypochlorite (on an "as is" basis), one may add about 0.022 weight percent sodium sulfite. Such an approximate 25 to 30 weight percent apparent excess is necessary because of induction effects. Indeed, it is preferred to retest a batch after antichlor addition to insure total elimination of bleach, usually as evidenced by a positive sulfite response; e.g., iodine consumption.

Once the absence of hypochlorite is evident it is preferred to adjust the pH of a batch to a level below a pH of about 12 with sulfuric acid or other acid.

While operating at higher temperatures generally reduces the efficiency of bleach in terms of maximizing the color change or reduction achieved (measured in terms of Klett numbers or the like) based on a given bleach charge, at higher temperatures, more bleaching can be obtained in a shorter time, although the amount of bleach required to achieve equivalent color reduction or lightening is somewhat greater than at lower temperatures. In other words, if one uses a higher temperature for bleaching than some prechosen lower temperature, more bleach will be needed to achieve an equivalent whitening action. However, a specified degree of whitening at such higher temperature will be achieved in a briefer time at higher temperatures.

In accord with the teachings of the invention, the hypochlorite bleaching conditions which minimize sultone reformation are those which are most efficient for color improvement. Efficiency here is meant to involve attainment of the best color for a given bleach charge. However, from a production processing time point-of-view, bleaching must be thought of as a "trade off." The best colors for a given bleach charge are attained at low to moderate temperatures, typically about 25° to 40° C., however, at the expense of processing time. From a compromise viewpoint, temperatures of about 40° to 50° C. are recommended. Temperatures of greater than about 50° C. may be used when processing time is at a premium. At higher temperatures, additional bleach will, in general, be required to reach a comparable color level attainable at a lower temperature with a definite amount of given bleach.

Hydrogen peroxide may be used as a bleaching agent for whitening a previously heated alkali metal alpha olefin sulfonated material. When so using hydrogen peroxide, the pH of the system should be about 9 or greater if buffers are employed to maintain pH. However, if buffers are not to be employed, the initial pH should be greater than about 12. In the latter case, that of no buffers, the pH will normally drop during hydrogen peroxide bleaching.

Turning to FIG. 1, there is seen a schematic diagram illustrating a preferred form for conducting a heating operation of this invention continuously. Here, an alkali metal hydroxide neutralized reaction product of mixed alpha olefins and sulfur trioxide in a neutralization tank 10 is pumped by pump 11 through pipes 12 and 13 to and through a heat exchanger 14 and out through a pipe 16 continuously. Material temperatures in tank 10 can range typically from about 40° to 60° C., whereas material temperatures exiting heat exchanger, sensed in pipe 16 by controller 17, can range typically from about 100° to 110° C. Controller 17 can be considered to generate a signal which is used to regulate a variable valve 18 is heating fluid (e.g. steam) input line 19 for heat exchange 14, so that the flow rate of heating fluid through heat exchanger 14 via input line 19 and output line 21 can be used to determine the temperature of material in pipe 16.

At T-connector 22, high pressure steam is injected into material exiting from pipe 16 into connector 22 and the resulting mixture progresses onwardly through pipe 24. A controller 26, for example, can sense temperature in pipe 24 and temperatures here can range, typically, from about 150° to 180° C. Controller 26 can be considered to generate a signal which is used to regulate a variable valve 27 in stream input pipe 23 so that the flow rate of steam from pipe 23 can be used to determine the temperature of material in pipe 24.

From the line 24 the material enters heat exchanger 28 whose tube interval diameters are enlarged so as to slow the flow rate of material therethrough so as to maintain such material in such heat exchanger 28 a desired residence time. Heat exchanger 28 may be jacketed and equipped with fluid input line 25 and fluid output line 30 to aid in maintaining a desired material temperature therein. From heat exchanger 28, such material exits through pipe 29 and passes into a flash tank 31. A controller 32, for example, can sense pressures in pipe 29. Controller 32 can be considered to generate a signal which is used to regulate a variable valve 33 in pipe 29. Thus, pressures upon material in heat exchanger 28 typically can range from about 120 to 160 psig, and typical residence times for material in heat exchanger 28 can typically range from about 15 to 40 minutes.

In flash tank 31, a significant portion of the steam charged through pipe 23 is vaporized and escapes through line 34. Steam in line 34, typically near atmospheric pressures, can be condensed. Pressures in flash tank 31 can be maintained, typically, at atmospheric levels.

Material in fluid form in the bottom portions of flash tank 31 is ported into a pipe 36 and is moved by a pump 37 into line 38. A controller 39 can sense the temperature of fluid material in pipe 36. Typically, the temperature ranges from about 100° to 105° C. Controller 39 can be considered to generate a signal which is used to regulate the speed at which the pump 37 operates so as to maintain a desired temperature level in flash tank 31. Material moved by pump 37 passes through pipe 38 into a heat exchanger 41 which operates to cool material passing therethrough and exiting therefrom through pipe 42. A controller 43, for example, can sense temperatures in pipe 42. Temperatures in pipe 42 typically can range from about 50° to 60° C. Controller 43 can be considered to generate a signal which is used to regulate a variable valve 44 in coolant input pipe 45 through shell and tube exchanger 41 and exiting through output pipe 45 can be used to regulate the temperatures of material passing through exchanger 41.

At T-connector 46, material flow proceeds either through pipe 47 or through pipe 48 depending upon which one of the line valves 51 and 49, respectively, is open. When, for example, valve 49 is closed and valve 51 is open, material flows through pipe 47 into bleach tank 52, which is equipped with an agitator (not shown). Either as tank 52 fills to some desired liquid level, or afterwards, aqueous bleach (sodium hypochlorite) is charged to tank 52 through line 53, the total quantity of bleach added being as earlier indicated herein. Tank 52 may be jacketed (not shown) to maintain a desired temperature environment. The bleaching conditions chosen are such as to permit a desired Klett color to be achieved within tank 52 within operating parameters.

After tank 52 is filled, valve 51 is closed and valve 49 is opened, and material passes through pipe 48 into bleach tank 54. Bleach (sodium hypochlorite) is charged to tank 54 through line 56 analogously to line 53 to tank 52. When bleaching of material in tank 52 is completed, and the contents are discharged through output line 57, to storage or the like as desired, and tank 52 then becomes available for refilling. Flow of fresh material into tank 52 is commenced again as valve 49 is closed and valve 51 is opened. Tanks 52 and 54 thus alternate in their duty cycles. Bleached material is discharged from tank 54 via line 58.

EMBODIMENTS

The present invention is further illustrated by reference to the following Examples. Those skilled in the art will appreciate that other and further embodiments are obvious and within the spirit and scope of this invention from the teachings of these present Examples taken with the accompanying specification.

EXAMPLE A

An alpha olefin sulfonate starting material for use in the following Examples is prepared by conventional prior art technology as follows:

The alpha olefin feedstock has a $C_{14}$ to $C_{16}$ weight ratio of about 2:1 and the chain length distribution is as follows for a weight percent total feedstock basis:

| Chain Length | |
|---|---|
| $C_{12}$ | 1.7 |
| $C_{14}$ | 65. |
| $C_{16}$ | 33.2 |
| $C_{18}$ | .1 |

On a total composition weight percentage basis, the feedstock has the following composition:

| Component | Weight percent |
|---|---|
| total olefin | 99.9 |
| paraffin | .1 |
| vinyl (alpha) | 77.6 |
| internal | 7.5 |
| branched (vinylidene) | 14.0 |

The average molecular weight is 205.

Figure 2:
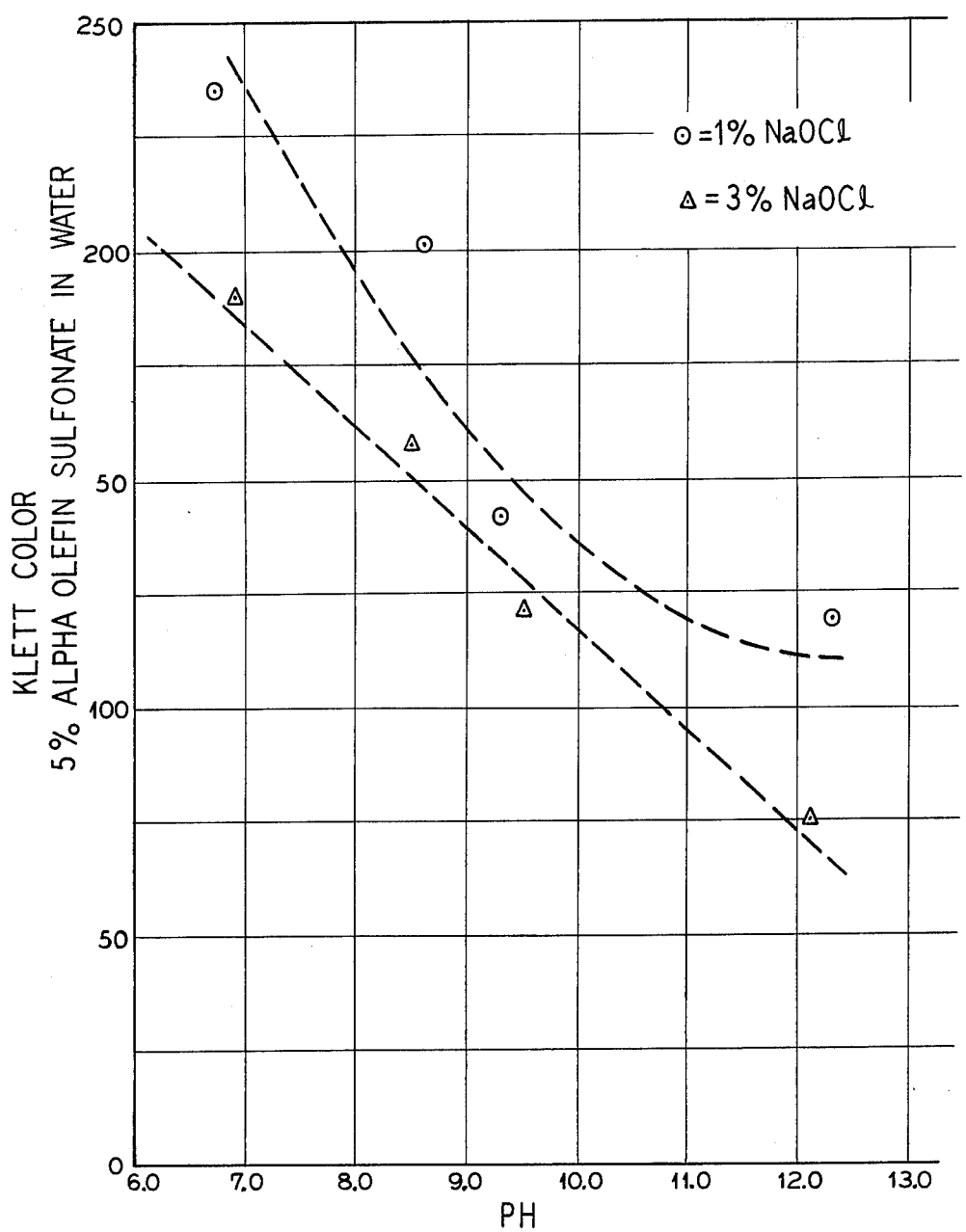

Using apparatus similar to that shown and described in FIGS. 1, 2 and 3 of Knaggs et al U.S. Pat. No. 3,169,142, this feedstock is reacted with an air-diluted stream of vaporized sulfur trioxide. The dilution volume percentage of $SO_3$ in the gaseous stream is about 4%. The $SO_3$ to feedstock mole ratio is about 1.08 moles $SO_3$ per mole of olefin feedstock. From the lower end of the reactor tube the alpha olefin/sulfur trioxide reaction product is collected and after a hold-up and in-transit residence time estimated to be about 15 minutes, the alpha olefin/sulfur trioxide reaction product is continuously charged to a continuously agitated aqueous neutralization bath containing initially about 6.25 weight percent (total weight basis) of sodium hydroxide which, during such charging, is maintained at the temperature range of about 45° to 55° C. After charging and neutralization is complete, the product mixture is found to comprise (on a 100 weight percent total weight basis):

| Component | Weight percent |
|---|---|
| alpha olefin sulfonates | about 39.4 |
| residual oil | about 5.0 |
| sodium hydroxide (Unreacted) | about 0.8 |
| sodium sulfate | about 0.8 |
| water | about 54 |

The residual oil is found to comprise (on a 100 weight percent total weight basis):

| Component | Weight percent |
|---|---|
| total olefins | about 16 |
| total sulfur-containing materials | about 80 |
| other | about 4 |

The total sulfur-containing material in such residual is found to comprise (on a 100 weight percent total weight basis):

| Component | Weight percent |
|---|---|
| mixed sultones | about 90 |
| mixed sulfonate esters | about 10 |

The residual oil content is determined by extraction with petroleum ether as hereinabove described.

The sultone content of the product mixture can be estimated by infrared spectroscopy, gas chromatography, or thin layer chromatography, though each such procedure involves isolation of the residual oil fraction of the product. Presently, the chromatographic techniques appear to provide the most sensitive estimation technique for low level measurements. By infrared spectroscopy, the 1,4-sultone content is initially estimated to be about 62 weight percent of the residual oil. However, the 1,4-sultone content of the neutralized material is observed to diminish with age (time).

The product mixture has a pH of greater than 13.1

EXAMPLE 1

A major portion of the product mixture of Example A (above) is heated to at least 113° to 116° C. under about 10 to 11 psig pressure for about 6 hours. (To help attain this temperature range more rapidly, some stream is injected into the product hydrolysis kettle.) During the hydrolysis period, sodium hydroxide is consumed by reaction with hydrolyzable sulfur-containing species. The product system contains at the termination of this period about 0.3 weight percent of unreacted, dissolved sodium hydroxide. The product mixture is found to comprise (on a 100 weight percent total basis):

| Component | Weight percent |
|---|---|
| Alpha olefin sulfonates | about 40.4 |
| Residual oil | about 1.0 |
| Sodium Hydroxide (unreacted) | about 0.3 |
| Sodium Sulfate | about 0.8 |
| Water | about 57.5 |

The residual oil is found to comprise (on a 100 weight percent total weight basis):

| Component | Weight percent |
|---|---|
| Total olefins | about 85 |
| Total sultones | if any, less than 0.05 |
| Other | about 15 |

The analysis for sultones is conducted by gas chromatography. (The lowest level of reliably detectable sultone values in the residual oil by gas chromatography is estimated to be at most about 0.05%. This equates to about 5 ppm on a total product basis.)

The product mixture has a Klett color of about 450 (based on a 5 weight percent solution of alpha olefin sulfonates in water).

EXAMPLE 2

The product mixture of Example 1 is cooled to about 45° C. and then about 1.6 weight percent (based on total weight of alkali metal sulfonated products present in product mixture of Example 1) of sodium hypochlorite (active ingredient) is added thereto with agitation. The sodium hypochlorite is in the physical form of an approximately 14% "active ingredient" aqueous solution. After the sodium hypochlorite addition is complete, the pH of the resulting solution is found to be about 12.7, and agitation is continued with the temperature being maintained at about 45° C. Samples of the reactant mixture are taken at intervals for Klett color analysis and sultone analysis. After about 4 hours, the reactant mixture is found to have a Klett color of about 100 (based upon 5 weight percent alpha olefin sulfonates in water). The residual (unreacted) hypochlorite content is found to be about 0.1% (total product basis). At no time during this contacting with sodium hypochlorite is found any evidence of reformation of sultones as measured by gas chromatographic analysis of extracted residual oil. The product mixture is found to comprise (on a 100 weight percent total weight basis):

| Component | Weight percent |
|---|---|
| alpha olefin sulfonates | about 38.5 |
| residual oil | about 1.0 |
| sodium hydroxide (Unreacted) | about 0.3 |
| sodium chloride | about 0.9 |
| sodium sulfate | about 0.8 |
| sodium hypochlorite | about 0.1 |

The residual oil is found to comprise (on a 100 weight percent total weight basis):

| Component | Weight percent |
|---|---|
| total olefins | about 85 |
| total sultones | if any, less than 0.05 |
| other | about 15 |

EXAMPLE 3

A portion of the product mixture of Example 2 is taken and is maintained with agitation at a pH of about 12.7 and at a temperature of about 45° C. until the residual sodium hypochlorite present has been completely consumed which requires a time of about 10 hours. The reactant mixture is found to have a Klett color of about 80 (based upon 5 weight percent alpha olefin sulfonates in water). Samples of the reactant mixture takes at intervals for sultone analysis reveal that at no time during this continued contacting with sodium hypochlorite is there any evidence of reformation of sultones. The product mixture is found to comprise (on a 100 weight percent total weight basis):

| Component | Weight percent |
|---|---|
| alpha olefin sulfonates | about 38.6 |
| residual oil | about 1.0 |
| sodium hydroxide (unreacted) | about 0.3 |
| sodium chloride | about 0.9 |
| sodium sulfate | about 0.8 |
| sodium hypochlorite | (none found) |

The residual oil is found to comprise (on a 100 weight percent total weight basis):

| Component | Weight percent |
|---|---|
| total olefins | about 85 |
| total sultones | if any, less than 0.05 |
| other | about 15 |

The sultone analysis is conducted as in Example 1.

EXAMPLE 4

The product of Example 3 is admixed with sufficient sulfuric acid (50% aqueous solution) to make the product pH be about 9. No sultone containing materials are found in the residual oil of the product. Color remains at the approximate value shown in Example 3.

EXAMPLE 5

A portion of the product mixture of Example 2 is taken and there is added thereto with agitation at a temperature of about 45° C. a sufficient quantity of sodium sulfite to substantially completely react with all residual sodium hypochlorite present. The product mixture is found to have a Klett color of about 100 (based upon 5 weight percent alpha olefin sulfonates in water). Samples of the reactant mixture taken at intervals for sultone analysis reveal that at no time during such sulfite reaction is there any sultone reformation. The product mixture is found to comprise (on a 100 weight percent total weight basis):

| Component | Weight percent |
|---|---|
| alpha olefin sulfonates | about 38.6 |
| residual oil | about 1.0 |
| sodium hydroxide (unreacted) | about 0.3 |
| sodium chloride | about 0.9 |
| sodium sulfate | about 1.0 |
| sodium hypochlorite | (none found) |
| sodium sulfite | traces |

The residual oil is found to comprise (on a 100 weight percent total weight basis):

| Component | Weight percent |
|---|---|
| total olefins | about 85 |
| total sultones | if any, less than 0.05 |
| other | about 15 |

The sultone analysis is conducted as in Example 1.

EXAMPLE 6

The product of Example 5 is admixed with sufficient sulfuric acid (50% aqueous solution) to make the product pH to about 9. No evidence of sultone reformation is found by analysis of the extracted residual oil of the resulting product and the product color remains at the approximate value shown in Example 5.

EXAMPLE 7

Referring to FIG. 1, an alpha olefin sulfonate starting material prepared as in Example A is discharged from neutralization tank 10 with pump 11 and is heated by heat exchanger 14 to a temperature of about 104° C. as measured by controller 17. Steam injection raises the temperature to about 160° C. as measured by controller 26. Material is retained in heat exchanger 28 for about 15 to 20 minutes at a temperature of about 160° C. with the pressure being maintained at about 130 psig by controller 32. After passage through flash tank 31, the material temperature is about 102° C. as measured by controller 39. After passing through heat exchanger 41, the material has a temperature of about 55° C. Material in either tank 52 or tank 54 is bleached in about 4 hours using a temperature of about 45° C. The pH of the starting material is greater than 13.1, and, in this example, the starting material contains about 0.8 weight percent excess unreacted dissolved NaOH and about 1.6 weight percent active NaOCl is added for bleaching (based on weight of alkali metal sulfonates present). The product after bleaching has a pH of about 12.7 and contains about 0.1 weight percent residual NaOCl (total weight basis). The product contains no measurable sultones in its residual oil. Total residual oil in product is about 1.0 weight percent (total weight basis).

EXAMPLE 8

To show the relationship between Klett color (at 5% sodium alpha olefin sulfonates in water) and bleaching pH, the following laboratory procedure is used:

Samples of the product mixture of Example 1 are taken. To each one of a first set of samples, 1 weight percent of NaOCl is added (based on total sodium alpha olefin sulfonate in water), each sample being adjusted to a different pH with suitable buffer, while maintaining the temperature at about 50° C. The time from initial addition of NaOCl until NaOCl content fell to not more than about 0.1 weight percent is measured.

To each one of a second set of samples 3.0 weight percent of NaOCl is added (same basis), each sample likewise being priorly adjusted to a different pH with suitable buffer while maintaining the temperature at about 50° C. The time for NaOCl consumption to the same level is similarly measured.

The results are shown in Table 1 below and in FIG. 2. The results show increased bleaching efficiency while using pH values as disclosed and claimed in this invention. The dotted lines in FIG. 2 are provided to show estimated slope only.

TABLE I

BLEACHING: COLOR VS. pH

| % NaOCl (on Active) | pH | Time* (Hrs.) | Temp- ° C. | Klett Color (5% Active) |
|---|---|---|---|---|
| 1.0 | 12.3 | 5 | 50 | 120 |
|  | 9.3 | 1 |  | 142 |
|  | 8.6 | < (1/12) |  | 202 |
|  | 6.7 | < (1/30) |  | 235 |
| 3.0 | 12.1 | 11ª | 50 | 76 |
|  | 9.5 | 1 to 2 |  | 122 |
|  | 8.5 | < (1/12) |  | 158 |
|  | 6.9 | < (1/30) |  | 190 |

*Time from initial addition of bleach until bleach content ≦ 0.1%
ªResidual bleach = 0.23%

The claims are:

1. In a process for making an alpha olefin sulfonate product by contacting a stream of vaporized sulphur trioxide in an inert gas mixture with alpha olefins containing from about 8 through 24 carbon atoms per molecule followed by admixture of the reaction product with aqueous alkali metal hydroxide to produce an aqueous mixture which comprises, on a 100 weight percent total weight basis at least about 52 weight percent water with the balance up to 100 weight percent comprising solids, said solids comprising, on a 100 weight percent dry basis, from about 50 to 90 weight percent of alkali metal salts of alpha olefin sulfonate, from about 5 to 40 weight percent dispersed residual oil, and the balance up to 100 weight percent being alkali metal hydroxide, the exact amount of alkali metal hydroxide present in any given system being sufficient to maintain a pH in said aqueous mixture greater than about 12, the improvement which is to substantially completely eliminate sultones from the final product and comprises the steps of A. heating such resulting aqueous mixture at a temperature of from about 95° to 190° C while maintaining said system under a pressure of from about atmospheric to about 230 p.s.i. for a time typically ranging from about 30 minutes to 8 hours but which is sufficient to substantially completely eliminate sultones from residual oil in said system, said heating being conducted while maintaining sufficient dissolved free alkali metal hydroxide present in said system to produce a system pH in the range of from about 12 to 14, B. cooling the resulting system to a temperature not above about 60° C, and C. contacting such cooled resulting system under liquid phase aqueous conditions with sodium hypochlorite bleaching agent, the total active ingredient amount of said bleaching agent used being from about 0.1 to 6 weight percent of the total weight of alkali metal sulfonates present in said resulting system, said contacting being conducted while maintaining said resulting system at a pH in the range of from about 12 to 14 and while maintaining a temperature of from about 25° to 60° C, said contacting being conducted for a time sufficient to produce a product having a Klett color based on 5 weight percent alpha olefin sulfonate in water of less than about 180, such bleaching substantially completely preventing reformation of sultones.

2. The process of claim 1 wherein said contacting is continued for a time sufficient to substantially completely consume said bleaching agent.

3. The process of claim 1 wherein, after said contacting, a measurable quantity of residual bleaching agent remains in the resulting product after said contacting is completed, and wherein there is admixed with such product at least a sufficient quantity of at least one reducing agent selected from the group consisting of sodium sulfite and sodium bisulfite to substantially completely react with such residual bleaching agent.

4. The process of claim 2 wherein, after said contacting, the resulting product is admixed with a sufficient quantity of an acid to make the pH of the resulting product system fall in the range of from about 7 to 12.

5. The process of claim 3 wherein, after such admixing with reducing agent, the resulting product is admixed with a sufficient quantity of an acid to produce in such product a pH in the range of from about 7 to 12.

6. The process of claim 2 wherein said alpha olefins contain from about 12 through 18 carbon atoms and such resulting product has a Klett color based on 5 weight percent alpha olefin sulfonate in water of less than about 130.

7. The process of claim 3 wherein said alpha olefins contain from about 12 through 18 carbon atoms and such resulting product has a Klett color based on 5 weight percent alpha olefin sulfonate in water of less than about 130.

8. The process of claim 1 wherein, after said heating and before said contacting, the quantity of dissolved-free alkali metal hydroxide present in said system falls in the range of from about 0.04 to 3.8 weight percent based upon total system weight and wherein said alkali metal hydroxide is sodium hydroxide.

9. The process of claim 1 wherein said heating is conducted batch-wise and wherein the temperature and pressure are such that said heating requires from about 4 to 8 hours for such substantial completion.

10. The process of claim 1 wherein said heating is conducted continuously and wherein temperature and the pressure are such that said heating require less than about 1 hour for such substantial completion.

11. The process of claim 1 wherein said heating is carried out at a temperature in the range from about 110° to 120° C.

12. The process of claim 1 wherein said contacting is carried out generally at a temperature in the range from about 150° to 180° C.

* * * * *